United States Patent [19]

Suzuki et al.

[11] Patent Number: 5,102,333
[45] Date of Patent: Apr. 7, 1992

[54] ORTHODONTIC PROCESS FOR STRAIGHTENING TEETH

[75] Inventors: Yuichi Suzuki; Fujio Miura; Ishi Miura, all of Tokyo, Japan

[73] Assignee: Furukawa Electric Company, Ltd., Tokyo, Japan

[21] Appl. No.: 635,399

[22] Filed: Dec. 27, 1990

Related U.S. Application Data

[60] Division of Ser. No. 71,556, Jul. 7, 1987, abandoned, which is a continuation of Ser. No. 854,075, Apr. 17, 1986, abandoned, which is a continuation of Ser. No. 716,269, Mar. 26, 1985, abandoned.

[30] Foreign Application Priority Data

Mar. 27, 1984 [JP] Japan .................................. 59-57401

[51] Int. Cl.⁵ ............................................... A61C 3/00
[52] U.S. Cl. ........................................ 433/24; 433/20
[58] Field of Search ..................................... 433/20, 24

[56] References Cited

U.S. PATENT DOCUMENTS 3,729,824  5/1973  Baues et al. .......................... 433/20
4,037,324  7/1977  Andreasen ............................ 433/24
4,490,112 12/1984  Tanaka et al. ........................ 433/20

*Primary Examiner*—John J. Wilson
*Attorney, Agent, or Firm*—Armstrong, Nikaido, Marmelstein, Kubovcik & Murray

[57] ABSTRACT

A process for straightening teeth using super-elastic NiTi arch wires of the same diameter but having different recovery forces is carried out by using NiTi wires that have a transition temperature below body temperature with brackets on the teeth. The different recovery force is set for each wire by heat treating the wires at different temperatures and/or for different periods of time. In this manner the forces applied to the teeth can be changed while still using arch wires of the same diameter.

2 Claims, 2 Drawing Sheets

5,102,333

ORTHODONTIC PROCESS FOR STRAIGHTENING TEETH

This application is a division of application Ser. No. 071,556 filed on 7/7/87 now abandoned which is a continuation of Ser. No. 854,075 filed on 4/17/86, now abandoned which is a continuation of Ser. No. 716,269 filed 3/26/85 now abandoned.

DETAILED DESCRIPTION OF THE INVENTION

This invention relates to a novel orthodontic system for the orthodontic movement of teeth.

Orthodontic systems to move malaligned teeth to desired positions generally involved, the attachment of brackets (2) to indiviual teeth (1) by means of bands which encircle the teeth or by adhesion, and the connection of orthodontic wire (3) to the brackets in order to create an orthodontic force to move the teeth toward desired position.

Conventional orthodontic systems have utilized orthodontic wire formed from stainless steel, Co—Cr based alloy or others. In these conventional wires, recovery range due to the elasticity of the wire is limited and the elastic modulas has a high value.

Accordingly, complicated procedures have evolved to enlarge the moving range of orthodontic wires. These include forming variously shaped loops between the brackets. In spite of such treatments, the orthodontic force still decreases gradually with the movement of the teeth. Readjustment and/or exchange of the orthodontic wire is necessary in conjunction with the progress of the orthodontic treatment. Furthermore, depending upon the degree and the stage of the orthodontic procedure, wires having various recovering forces must be adapted to the degree and stage as required. Consequently, a lot of components, such as orthodontic wires of different sizes with brackets fitted thereto, and others, have been necessitated. The orthodontic procedure, therefore, became complicated. In order to resolve these problems, a method has been developed which utilizes an excellent shape recovery force based on the shape memory effect of Ni—Ti base alloys. These alloys have composition of the stoichiometric intermetallic compound, the atomic ratio of Ni and Ti on 1:1, and they undergo thermoelastic martensitic transformation. The method utilizes the shape memory effect which is a specific phenomena caused by said transformation. Namely, the alloy memorized a desired shape at a high temperature. When it is deformed at a temperature below the transformation temperature, the wire recovers the original shape when heated to a temperature above the transformation temperature. The method applies this recovery force to the orthodontic procedure. This allows the number of times necessary to adjust and set the wire to be reduced. Moreover, this alloy has additional advantages in that the corrosion resistance and biocompatibility are excellent. However, even in case of the shape memory wires, various sizes wires should be prepared to obtain appropriate orthodontic forces corresponding to the degree and the stage of the orthodontic treatment. Accordingly, the number of components, such as brackets, cannot be reduced, and the complication is not greatly improved.

As a result of the various investigations, the inventors have studied that the recovery force due to the super elasticity can be adjusted by heat treatment. Super elasticity is one of the unique phenomena caused by the aforementioned Ni—Ti base alloy which appears at a temperature above the martensitic transformation temperature. The inventors have developed a orthodontic system for teeth in which a simplified procedure is made possible by using orthodnotic wires of a single size or of only a few kinds of sizes at almost all stages. That is, the invention involves brackets which attach to the teeth and orthodontic wires connecting to the brackets, and subject forces to the teeth which move the teeth toward desired positions. The orthodontic wire of the invention comprising a super elastic Ni—Ti base alloy in which the recovery force is adjusted by heat treatment.

Namely, the invention utilizes wire consisting of superelastic Ni—Ti base alloy which has excellent corrosin resistance and good biocompatibility and provides desired recovery force adapted for the state of the orthodontic treatment by the heat treatment. Accordingly, the invention succeeds in the orthodontic procedure with wires of a single size or of only a few-kinds of sizes.

Superelasticity is a property which causes the wire to recover its original shape, as with rubber, even when deformed beyond its elastic limit. In ordinary metal material, plastic deformation takes place when the metal is deformed beyond the elastic limit and only a portion of the elastic deformation, which is as much as 0.5% at most, recovers when unloaded. On the contrary, the superelastic alloy can recover its original shape at unloading even when strained to 10% deformation. The recovery force with the superelasticity is decreased by the heat treatment, in which the degree of decrement is larger when the temperature is higher and the time is longer. Accordingly, the recovery force can be controlled arbitrarily by selecting the temperature and the time of heat treatment.

When the superelastic Ni—Ti base alloy is utilized for this purpose, it is required that the transformation temperature of the alloy be settled lower than the body temperature. To achieve such a transformation temperature, a composition ratio of Ni and Ti is selected within a range of 50.0 to 51.0% of Ni and the remainder of Ti, or a small amount lower than 0.5% of either one or both of Ni and Ti within a range of said composition is substituted by either one or more than two of the elements such as Co, Cr, Fe, etc. The transformation temperature of the super-elastic Ni—Ti base alloy is extremely sensitive to the composition thereof, and it can be lowered with the slight variance of the composition.

Heat treatment to adjust the recovery force comprises forming the superelastic Ni—Ti base alloy wire in a linear shape or an arch shape to fit the teeth, and then heat treating by an appropriate method, such as the heating temperature of 300° to 600° C. and a heating time of a few seconds to several hours in atmosphere and in inert gas. In particular, electric heating is convenient. This heating method adjusts the recovery force locally in the manner of varying with axial position by position dependent heat treatment. Furthermore, the wire can be bent to a desirable curvature at the time of heat treatment.

BRIEF DESCRIPTION OF THE DRAWINGS

FIG. 1 and FIG. 6 illustrate an example of the orthodontic system of teeth, wherein FIG. 1 is a side view and FIG. 6 is a ground plan.

Figure 1:
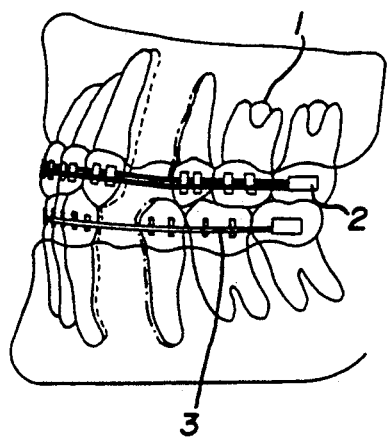
Figure 6:
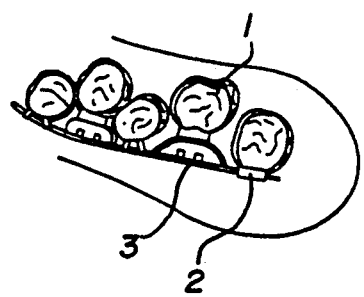

1.—Tooth
2.—Bracket
3.—Orthodontic wire
4, 4' 5—bar

The invention will be presented in detail using examples.

An alloy comprising 51% of Ni and the remainder of Ti was melted and casted in vacuum. An ingot was forged and hot rolled and then cold drawn. Intermediate annealing was repeated during the drawing process. The alloy was finally finished to a wire of 0.4 mm diameter.

Figure 2:
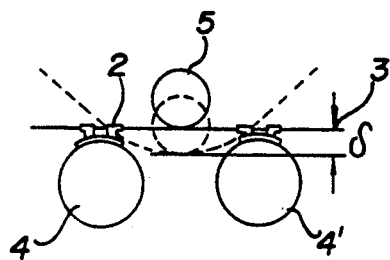
FIG. 2 illustrates an example of the measuring methods of the recovery force of orthodontic wire.
Figure 3:
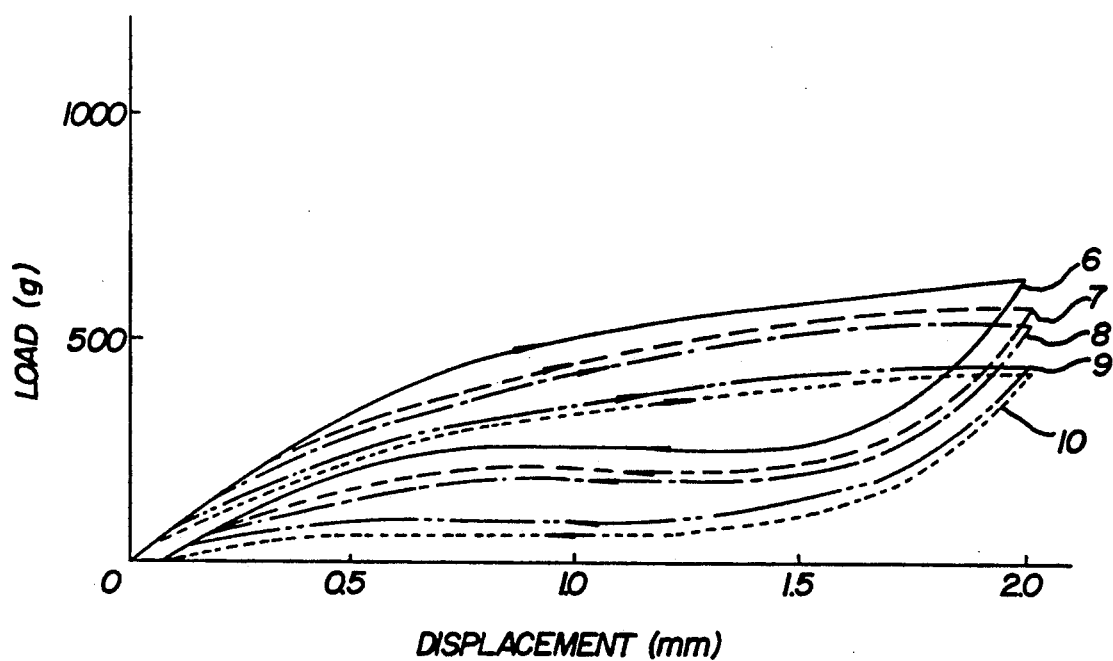
FIG. 3 through FIG. 5 are diagrams of the load-deflection curves, respectively, which show the relationship between the heat treatment and the recovery force of orthodontic wire of the invention.
Figure 4:
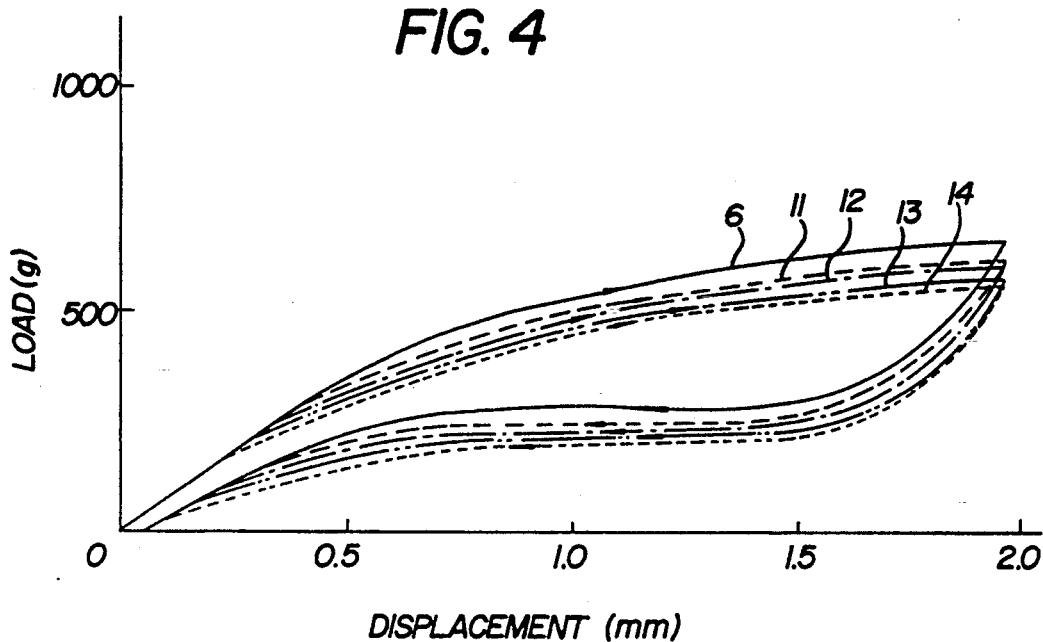
Figure 5:
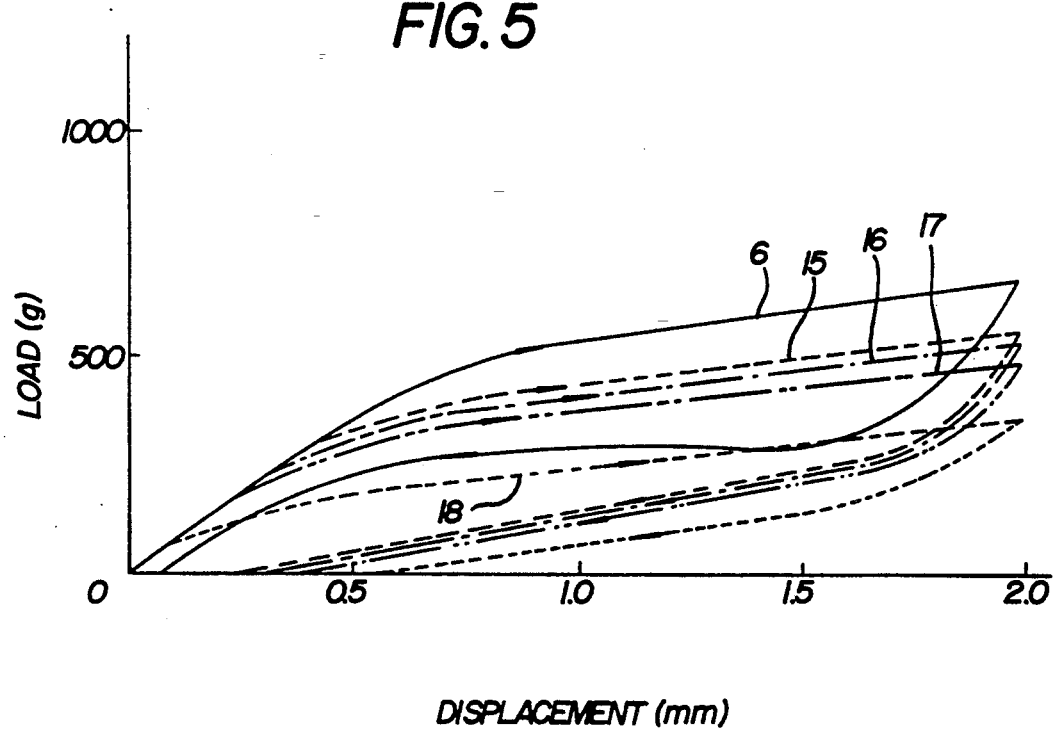

After the scales on the surface were removed, the wire material was fixed in a linear shape and subjected to heat treatment, the recovery force of the wire was evaluated as follows: As shown in FIG. 2, a pair of bars (4) (4') with a diameter of 7 mm were placed oppositely so as to the distance between centers being 14 mm, the brackets (2) were settled on said bars (4) (4'), and the orthodontic wire (3) was fitted. Load was applied to the middle point of the wire through a round bar (5) with a diameter of 5.0 mm, and the recovery force was estimated by the flexure ($\delta$). Results are shown in FIG. 3 through FIG. 5. This measurement simulates an orthodontic procedure of a portion from canine to premolar.

The figures show the load-deflection curves. A curve of the alloy wire which was subjected to the straightening treatment in intermediate temperature after cold drawing is cited as (6) in FIG. 3. Curves of the wires which were heat treated at 500° C. for 5, 10, 60 and 120 minutes, are cited as (7), (8), (9) and (10) respectively. Curves cited as (11), (12), (13) and (14) in FIG. 4 are those of wires subjected to the heat treatment at 400° C. for 5, 10, 60 and 120 minutes, respectively. Curves of (15), (16), (17), and (18) in FIG. 5 are of wires subjected to the heat treatment at 600° C. for 5, 10, 60 and 120 minutes respectively.

The figures show clearly that the superelastic Ni—Ti base alloy wires can recover its very large displacement with a constant force and stress at loading (arrow indicating upward) and unloading (arrow indicating downward) are. For the orthodontic treatment of the teeth, the stress at unloading, that is, the recovery force is important, and this recovery force varys with both heat treatment temperature and treatment time. Therefore, desired recovery force can be obtained by selecting these conditions appropriately. The recovery force of the flat portion at unloading is changed from 270 g of No. 6 to 220 g by the heat treatment at 500° C. for 5 minutes (No. 7). The recovery force further varys to 200 g, 100 g and 65 g with the treatment for 10 (No. 8), 60 (No. 9) and 120 (No. 10) minutes, respectively. Recovery forces of the wires treated at 400° C. for 5 (No. 11), 10 (No. 12), 60 (No. 13) and 120 (No. 14) minutes are 250 g, 230 g, 200 g and 190 g, respectively. In the case of the wires treated at 600° C. for 5 (No. 15), 10 (No. 16), 60 (No. 17) and 120 (No. 18), the flat portions are not observed because of a certain amount of residual deformation, although the recovery behaviors corresponding to the treatment times is indicated.

In above, the description was made with regard to the linear shape orthodontic wire, but the invention is not confined to this. For example, the recovery force can also be adjusted by the heat treatment after or at a time of forming an arch shape. The recovery force can also be adjusted by the heat treatment. The wire is attached to the brackets attached to the teeth to connect them, and, at this time, the curvature of the arch can be adjusted after heat treatment to disired recovery force. Also, the recovery force can be adjusted through the formation of a bend between respective brackets. These operations can be conducted separately from the heat treatment or at the same time as the heat treatment. Particularly, when using electric heating, both ends or appropriate intermediate portions of the wire are grasped with two or more pliers while providing electric current between the pliers and at this time the wire can be deformed to desired shape.

As described above, according to the invention, the recovery force of the orthodontic wire can be adjusted to the desired strength arbitrarily. Accordingly, not only the wire of the invention provides orthodontic procedure with the recovery force fit for the state of the treatment, but also a constant recovery force which does not decrease with the progress in the orthodontic treatment. Moreover, the number of times to exchange or reattach the wire is reduced markedly and, the size of the bracket depending upon the size of the wire is also reduced. As a result, complication in orthodontic procedure is relieved significantly. Furthermore, the recovery force can be adjusted locally, that is, can be strengthened or weakened against individual tooth, such special treatment are exerted as the teeth intended for the treatment can be treated selectively, and so on.

What is claimed is:

1. A process for reducing the number of different diameter super—elastic NiTi—based wires used in association with brackets affixed to teeth, for straighening said teeth, which comprises:

heat treating a first super—elastic NiTi—based wire, having a transition temperature below body temperature and having a fixed diameter, at a first temperature and for a first time period to create a wire having a certain recovery force;

applying said wire to said brackets on the teeth to move the teeth with said recovery force heat treating a second super—elastic NiTi—based wire having the same transition temperature and the same diameter as the wire of step 1 and heating the second wire at a different temperature or for different time to create a second wire having a recovery force different than the first wire and removing said first wire and applying said second wire to the teeth to continue moving the teeth with said different recovery force.

2. The process of claim 1 wherein said first and second heat treatments are conducted at temperatures between 300°–600° C. for a period of 5 to 120 minutes.

* * * * *